United States Patent
Schelling et al.

(10) Patent No.: US 10,252,912 B2
(45) Date of Patent: Apr. 9, 2019

(54) SEPARATION OF A PHOSGENE- AND HYDROGEN CHLORIDE-COMPRISING STREAM

(71) Applicant: BASF SE, Ludwigshafen (DE)

(72) Inventors: Heiner Schelling, Bobenheim am Berg (DE); Torsten Mattke, Freinsheim (DE); Hans-Juergen Pallasch, Kallstadt (DE); Kai Thiele, Antwerp (BE)

(73) Assignee: BASF SE, Ludwigshafen (DE)

( * ) Notice: Subject to any disclaimer, the term of this patent is extended or adjusted under 35 U.S.C. 154(b) by 16 days.

(21) Appl. No.: 15/557,187

(22) PCT Filed: Mar. 10, 2016

(86) PCT No.: PCT/EP2016/055154
§ 371 (c)(1),
(2) Date: Sep. 11, 2017

(87) PCT Pub. No.: WO2016/142475
PCT Pub. Date: Sep. 15, 2016

(65) Prior Publication Data
US 2018/0044179 A1    Feb. 15, 2018

(30) Foreign Application Priority Data
Mar. 12, 2015    (EP) .................................... 15158862

(51) Int. Cl.
*C01B 7/07*    (2006.01)
*C01B 32/80*    (2017.01)
(Continued)

(52) U.S. Cl.
CPC .......... *C01B 7/0731* (2013.01); *B01D 53/002* (2013.01); *C01B 7/0712* (2013.01);
(Continued)

(58) Field of Classification Search
CPC ..... C01B 7/0712; C01B 7/0731; C01B 53/80; C07C 263/10; C07C 263/20; B01D 53/002; F25J 3/00
See application file for complete search history.

(56) References Cited

U.S. PATENT DOCUMENTS

| 3,544,611 A | 12/1970 | Michelet et al. |
| 6,719,957 B2 | 4/2004 | Brady, Jr. et al. |

(Continued)

FOREIGN PATENT DOCUMENTS

| DE | 10 2004 026 095 A1 | 12/2005 |
| EP | 0 876 335 A1 | 11/1998 |

(Continued)

OTHER PUBLICATIONS

U.S. Appl. No. 15/305,923, filed Oct. 21, 2016, US 2017/0036997A1, Manfred Heilig, et al.

(Continued)

*Primary Examiner* — Brian A McCaig
(74) *Attorney, Agent, or Firm* — Oblon, McClelland, Maier & Neustadt, L.L.P.

(57) ABSTRACT

The invention relates to a method of separating a phosgene- and hydrogen chloride-comprising stream (5), wherein said method comprises conveying the hydrogen chloride- and phosgene-comprising stream (5) into a distillation column (1), withdrawing at the bottom of the distillation column (1) a phosgene-comprising stream (7) and withdrawing at the top of the column an essentially hydrogen chloride-comprising stream (9). At least a portion of the stream (9) withdrawn at the top is compressed and at least partially condensed and at least a portion of the liquid and compressed essentially hydrogen chloride-comprising stream is decompressed and recycled into the top of distillation column (1) as reflux.

9 Claims, 4 Drawing Sheets

(51) Int. Cl.
  *B01D 53/00* (2006.01)
  *C07C 263/10* (2006.01)
  *C07C 263/20* (2006.01)
  *F25J 3/00* (2006.01)

(52) U.S. Cl.
  CPC ............ *C01B 32/80* (2017.08); *C07C 263/10* (2013.01); *B01D 2257/2045* (2013.01); *C07C 263/20* (2013.01); *F25J 3/00* (2013.01)

(56) References Cited

U.S. PATENT DOCUMENTS

| | | | |
|---|---|---|---|
| 2006/0123842 A1* | 6/2006 | Sohn | C01B 7/0712 62/617 |
| 2007/0293707 A1 | 12/2007 | Wolfert et al. | |
| 2014/0147373 A1 | 5/2014 | Mouazer et al. | |

FOREIGN PATENT DOCUMENTS

| | | | |
|---|---|---|---|
| EP | 1 849 767 A1 | 10/2007 |
| EP | 1 981 619 A1 | 10/2008 |
| EP | 2 021 275 A2 | 2/2009 |
| EP | 2 559 658 A1 | 2/2013 |
| WO | WO 97/24320 A1 | 7/1997 |
| WO | WO 2004/056758 A1 | 7/2004 |
| WO | WO 2006/029788 A1 | 3/2006 |
| WO | WO 2008/122363 A1 | 10/2008 |
| WO | WO 2013/026591 A1 | 2/2013 |

OTHER PUBLICATIONS

Extended European Search Report dated Sep. 2, 2015 in Patent Application No. 15158862.1 (with English translation of categories of cited documents).
International Search Report dated Apr. 11, 2016 in PCT/EP2016/055154 (with English translation).
International Preliminary Report on Patentability dated Feb. 24, 2017 in PCT/EP2016/055154 filed Mar. 10, 2016 (with English translation).

* cited by examiner

SEPARATION OF A PHOSGENE- AND HYDROGEN CHLORIDE-COMPRISING STREAM

The invention relates to a method of separating a phosgene- and hydrogen chloride-comprising stream, wherein said method comprises conveying the hydrogen chloride- and phosgene-comprising stream into a distillation column, withdrawing at the bottom of the distillation column a phosgene-comprising stream and withdrawing at the top of the column an essentially hydrogen chloride-comprising stream.

Phosgene- and hydrogen chloride-comprising streams are generated, in particular, in the work-up of product streams from isocyanate production in a phosgenation.

This comprises contacting the corresponding amine with a stoichiometric excess of phosgene and reacting said amine to afford isocyanate and hydrogen chloride. Phosgenation may be carried out in a very wide variety of ways, for example as a gas phase phosgenation, cold-hot phosgenation, single-stage liquid phosgenation, hydrochloride phosgenation or gas/liquid phosgenation. Relevant methods are described, for example, in Ullmann's Encyclopedia of Industrial Chemistry, Chapter "Isocyanates, Organic", Chapters 4.1 and 4.2 (Six, C. and Richter, F., 2003). Inert media or solvents may be used depending on the type of method employed. The reaction mixture comprises essentially the isocyanate or precursors thereof, for example carbamyl chlorides, the hydrogen chloride formed, the excess phosgene and any inert media and/or solvents added.

The hydrogen chloride is removed from the product mixture substantially simultaneously with the excess phosgene irrespective of the type of work-up. Inert media and/or solvents are sometimes removed concurrently.

There is a very wide variety of uses for the hydrogen chloride reaction product. For instance, the hydrogen chloride may be subjected to oxidative dehydrogenation, for example by the Deacon or Kelchlor processes, or to electrolysis, to obtain chlorine for the synthesis of fresh phosgene. The hydrogen chloride may further be used in oxychlorinations. Absorption in water to obtain aqueous hydrochloric acid is also possible. This is described, for example, in Ullmann's Encyclopedia of Industrial Chemistry, "Isocyanates, Organic", Chapter 5 (Six, C. and Richter, F., 2003), WO-A 97/24320 and EP-A 0 876 335. In each case, the hydrogen chloride should initially be separated from the excess phosgene. Due to the sometimes significant excesses employed, recovery of the phosgene and return thereof into the process is necessary to ensure the very economic viability of the methods. Separation of hydrogen chloride and phosgene is therefore an essential component of isocyanate methods based on phosgenation. The above-described separation may be achieved using a very wide variety of thermal separation methods. Absorption and distillation are the most commonly used. Other methods such as membrane methods are disclosed in WO-A 2013/026591 for example.

Absorption comprises using an absorption medium to scrub out phosgene from a hydrogen chloride- and phosgene-comprising gaseous feed stream. Methods employing solvent often use said solvent as absorption medium. Such methods are described in EP-A 1 849 767 for example. However, one disadvantage of this method is that the hydrogen chloride comprises traces of the often organic absorption medium and said traces may cause problems when the hydrogen chloride is used in the Deacon process or in electrolysis for example. Where necessary the absorption medium needs to be removed from the hydrogen chloride in further thermal separation steps such as adsorption, for example as described in EP-A 1 981 619 and WO-A 2008/122363, or distillation/rectification, as described in U.S. Pat. No. 6,719,957 and EP-A 2 021 275 for example. A further disadvantage of absorption is the large fraction of absorption medium in the scrubbed-out phosgene and also fractions of dissolved hydrogen chloride which are likewise scrubbed out at the same time and may have a detrimental effect when the stream is returned to the reaction, as disclosed in DE-A 10 2004 026 095 for example. A further separation step before or after absorption may therefore become necessary to minimize both the hydrogen chloride content in the recycled phosgene and the proportion of absorption medium.

The above-described disadvantages of absorption may be avoided by a distillative separation of hydrogen chloride and phosgene. The large boiling-point difference between hydrogen chloride and phosgene permits distillative separation but, due to the high vapor pressure of hydrogen chloride, necessitates separation at low overhead temperatures or a correspondingly high pressure.

Low temperatures entail high capital expenditure and operating costs for a corresponding refrigeration plant. High pressure generally necessitates compression of the reaction gases or at least of portions thereof or a correspondingly higher pressure in the reaction. The latter may be detrimental to yield and quality. The compression of hydrogen chloride/phosgene gas mixtures presents great challenges in terms of safety, capital expenditure and operating costs.

It is an object of the invention to avoid the above-described disadvantages of the prior art methods for separating hydrogen chloride/phosgene mixtures.

This object is achieved by a method of separating a phosgene- and hydrogen chloride-comprising stream, wherein said method comprises conveying the hydrogen chloride- and phosgene-comprising stream into a distillation column, withdrawing at the bottom of the distillation column a phosgene-comprising stream and withdrawing at the top of the distillation column an essentially hydrogen chloride-comprising stream and compressing and at least partially condensing at least a portion of the stream withdrawn at the top and decompressing and recycling into the top of the distillation column as reflux at least a portion of the liquid and compressed essentially hydrogen chloride-comprising stream.

Compressing at least a portion of the essentially hydrogen chloride-comprising stream withdrawn at the top of the column allows the condensation to be carried out at relatively high temperatures with an attendant distinct reduction in energy consumption. Compression is typically avoided as far as possible since compression is associated with high energy requirements. A typical further goal is to handle phosgene at moderate pressures. A consequence of this is that, typically, compression of the crude gas stream of phosgene and hydrogen chloride is eschewed and an absorptive separation using a solvent is employed. In conventional methods, the operating pressure chosen therefor is the pressure at which the gaseous mixture arrives in the method.

The stream supplied to the distillation column derives, for example, from isocyanates production from the corresponding amine and phosgene. This isocyanate production may be carried out either in the gas phase or in the liquid phase. In the case of gas-phase phosgenation, the stream generally comprises hydrogen chloride and phosgene and any low-boiling secondary components or impurities. In the case of liquid-phase phosgenation, the stream may further comprise solvent.

The distillation of the phosgene- and hydrogen chloride-comprising stream is preferably carried out at the pressure at which the stream was withdrawn from isocyanate production. Suitable values for this pressure are generally in the range of from 1 to 10 bar (abs), preferably in the range of from 1.2 to 8 bar (abs) and in particular in the range of from 1.5 to 7 bar (abs).

Accordingly, the stream withdrawn at the top of the distillation column is obtained at a pressure equal to the pressure at which the distillation column is operated. The stream withdrawn at the top of the distillation column is preferably compressed to a pressure in the range of from 5 to 25 bar, more preferably to a pressure in the range of from 7 to 22 bar and in particular to a pressure in the range of from 10 to 20 bar.

In one embodiment of the invention the distillation column comprises a rectifying section and a stripping section and the phosgene- and hydrogen chloride-comprising stream is supplied as side feed between the rectifying section and the stripping section. Use of a distillation column with a rectifying section and a stripping section achieves improved purification of the phosgene obtained at the bottom. In particular this renders the phosgene obtained at the bottom substantially free of hydrogen chloride. In this context, substantially free is to be understood as meaning that the fraction of hydrogen chloride is in the range of from 10 to 1000 ppm. This allows the phosgene to be recycled into the isocyanate production directly and without further work-up while the absence of hydrogen chloride has the effect that commencement of undesired amine hydrochloride by-products formation occurs only after a delay rather than as soon as the amine is mixed with the phosgene which has the further advantage that the amount of amine hydrochloride formed is kept lower than when phosgene still comprising residual hydrogen chloride is added.

When a distillation column comprising only a rectifying section is employed rather than a distillation column comprising a rectifying section and a stripping section, the phosgene- and hydrogen chloride-comprising stream is fed into the bottom of the distillation column.

Independently of one another, the rectifying section and, where present, the stripping section preferably comprise internals, for example structured packings, random packings or trays, such as may be used in distillation columns. However, it is preferable to use one or more packings as internals in the rectifying section and in the stripping section.

In order to improve the purification of the essentially hydrogen chloride-comprising stream withdrawn at the top of the distillation column, it is advantageous when after compression the essentially hydrogen chloride-comprising stream withdrawn at the top is supplied to a rectifying column and the stream obtained at the bottom of the rectifying column is recycled into the top of the distillation column. It is preferable when the stream obtained at the top of the rectifying column is partially condensed in a condenser, the condensed portion is recycled into the rectifying column and the portion comprising uncondensed gaseous purified hydrogen chloride is withdrawn and sent for further use, for example in hydrochloric acid production or chlorine production by oxidation of the hydrogen chloride.

When the rectifying section of the distillation column is sufficiently dimensioned the rectifying column on the high-pressure side of the compressor may be dispensed with. All that is still required then is condensation of the fraction of hydrogen chloride required for the liquid reflux into the distillation column operated at lower pressure.

It is preferable to employ heat integration measures to conserve energy. Particularly the cold, uncondensed gas stream from the top condenser lends itself to heat integration. Said stream may be utilized for pre-cooling other streams. The cold stream obtained at the top of the column is also usable for energy integration measures. It is also conceivable to use intermediate cooling to minimize energy costs. The opportunities for energy integration and hence for minimizing energy consumption are manifold and are known to those skilled in the art.

In one embodiment, in a heat transferor the condensed and essentially hydrogen chloride-comprising stream gives off heat to the hydrogen chloride-comprising stream that is to be condensed, this giving-off of heat occurring before said stream is compressed. After compression, the hydrogen chloride-comprising stream is cooled down and partially condensed and the uncondensed portion is withdrawn via a gas takeoff. The condensed portion is recycled into the heat transferor as heat-transfer medium for heating the essentially hydrogen chloride-comprising stream withdrawn at the top.

In a further embodiment, in a heat exchanger the uncondensed portion of the essentially hydrogen chloride-comprising stream absorbs heat from the compressed and hydrogen chloride-comprising stream that is to be condensed. The hydrogen chloride-comprising stream to be condensed is thus pre-cooled before said stream is supplied to the condenser.

In a further possible version, a gas stream is withdrawn from the distillation column via a side takeoff, said stream is at least partially condensed in a first cooler, the liquid fraction is recycled into the distillation column and the gaseous portion is supplied to a second cooler, wherein in the second cooler the gas stream gives off heat to the essentially hydrogen chloride-comprising stream withdrawn from the top. It is preferable when the stream withdrawn at the top is heated up in a heat transferor before being supplied to the second cooler. It is preferable for the sake of effective utilization of energy when in the heat transferor the stream withdrawn from the top absorbs heat from the condensed stream recycled into the top of the distillation column.

Each of the individual heat integration measures described hereinabove may be implemented individually or in any desired combination.

Some examples of possible embodiments are shown in the figures and are more particularly described in the description which follows.

FIG. 1 shows the method according to the invention in a first embodiment.

Figure 1:
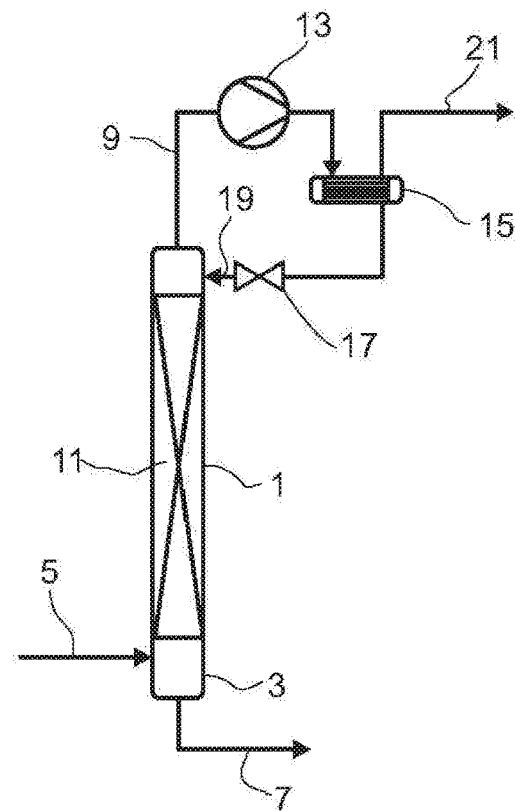
FIG. 1 shows a first embodiment of the method according to the invention.

A phosgene- and hydrogen chloride-comprising gaseous stream is supplied to lower region 3 of distillation column 1 via feed 5. In the distillation column, the phosgene- and hydrogen chloride-comprising stream is distillatively separated into a phosgene-comprising bottoms stream withdrawn via bottom takeoff 7 and an essentially hydrogen chloride-comprising stream withdrawn at top takeoff 9.

The phosgene- and hydrogen chloride-comprising stream preferably derives from isocyanate production. In one embodiment the pressure at which the distillation is performed is equal to the pressure at which the phosgene- and hydrogen chloride-comprising stream was withdrawn from isocyanate production. In an alternative embodiment the distillation is performed at a pressure below the pressure at which the phosgene- and hydrogen chloride-comprising stream was withdrawn from isocyanate production.

To aid distillation, distillation column 1 comprises internals 11, for example a structured packing or a random packing. Distillation column 1 may alternatively be a tray column.

In accordance with the invention the essentially hydrogen chloride-comprising stream withdrawn via top takeoff 9 is compressed to a higher pressure in compressor 13. The pressure to which the stream comprising essentially hydrogen chloride is compressed is preferably in the range of from 5 to 25 bar.

After compression, the essentially hydrogen chloride-comprising stream is passed into top condenser 15. The essentially hydrogen-chloride comprising stream is partially condensed in the top condenser. Due to the high pressure, this partial condensation does not necessitate cooling to temperatures that would be necessary had the condensation been carried out at the pressure prevailing at the top of the distillation column. The condensed portion of the essentially hydrogen chloride-comprising stream is decompressed in decompression means 17, for example a throttle or a valve, to the pressure prevailing at the top of distillation column 1. This stream thus cools down, while undergoing partial evaporation, to its boiling temperature at column pressure and is recycled into the top of distillation column 1 via return 19. The uncondensed portion of the essentially hydrogen chloride-comprising stream is withdrawn from top condenser 15 via gas takeoff 21.

Figure 2:
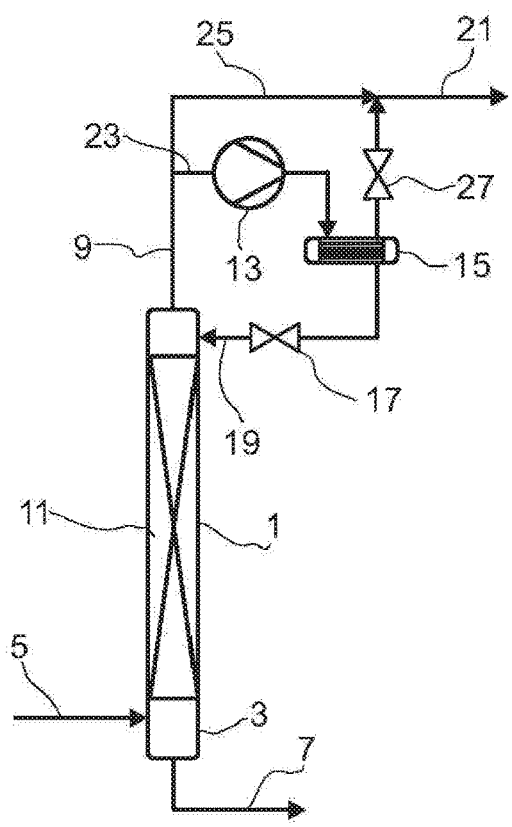
FIG. 2 shows a second embodiment of the method according to the invention.

FIG. 2 depicts a second embodiment of the method according to the invention.

In contrast to the embodiment depicted in FIG. 1, in the embodiment depicted in FIG. 2 the essentially hydrogen chloride-comprising stream withdrawn via top takeoff 9 is divided into first substream 23 and second substream 25. First substream 23 is supplied to compressor 13, compressed therein to the higher pressure and partially condensed in top condenser 15. Here too, the condensed portion of the essentially hydrogen chloride-comprising stream is decompressed in decompression means 17 and recycled into distillation column 1 via return 19. The gaseous fraction is decompressed in second decompression means 27 and withdrawn from the process. To this end, it is particularly preferable when—as depicted in FIG. 2—the decompressed gaseous fraction is introduced into second substream 25 and both the gaseous fraction and second substream 25 are discharged from the process via common gas takeoff 21.

First substream 23 preferably comprises from 5 to 50 vol %, in particular from 10 to 40 vol %, of the essentially hydrogen chloride-comprising stream withdrawn via top takeoff 9.

Figure 3:
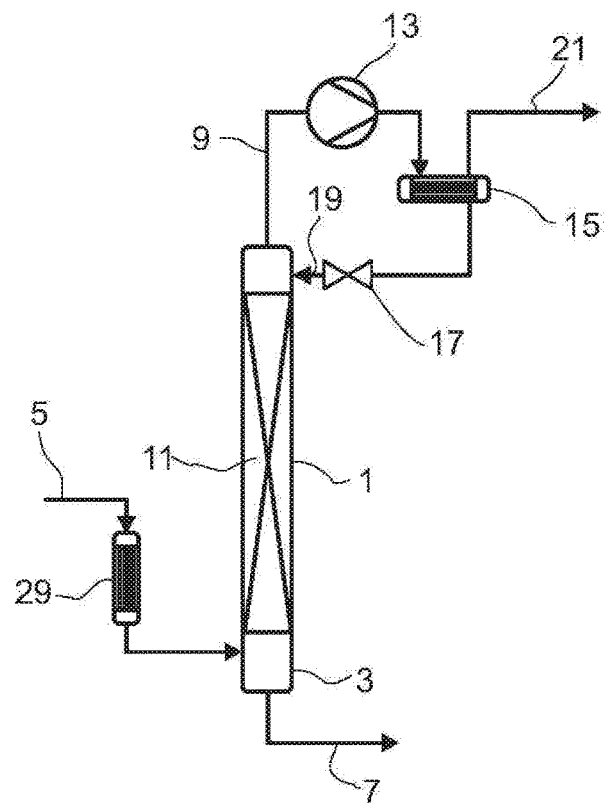
FIG. 3 shows the method according to the invention with pre-cooling/partial condensation of the phosgene- and hydrogen chloride-comprising stream to be supplied.

A further embodiment of the method according to the invention is depicted in FIG. 3. In contrast to the embodiment depicted in FIG. 1, in the embodiment depicted in FIG. 3 the phosgene- and hydrogen chloride-comprising stream to be supplied is pre-cooled in a single- or multi-stage procedure and/or partially condensed.

To this end, the phosgene- and hydrogen chloride-comprising stream is supplied to one or more heat exchangers 29 in which said stream is pre-cooled and/or partially condensed. The heat exchangers 29 are preferably indirect heat exchangers in which heat is given off to a suitable heat-transfer medium from the phosgene- and hydrogen chloride-comprising stream. Typically employed heat transfer media are thermal oils for example. Heat integration with other process streams is also possible.

In the embodiment depicted in FIG. 3 too, it is alternatively possible, as in the embodiment depicted in FIG. 2, to supply to top condenser 15 only a portion of the essentially hydrogen chloride-comprising stream withdrawn via top takeoff 9 rather than the entire essentially hydrogen chloride-comprising stream withdrawn via top takeoff 9.

Figure 4:
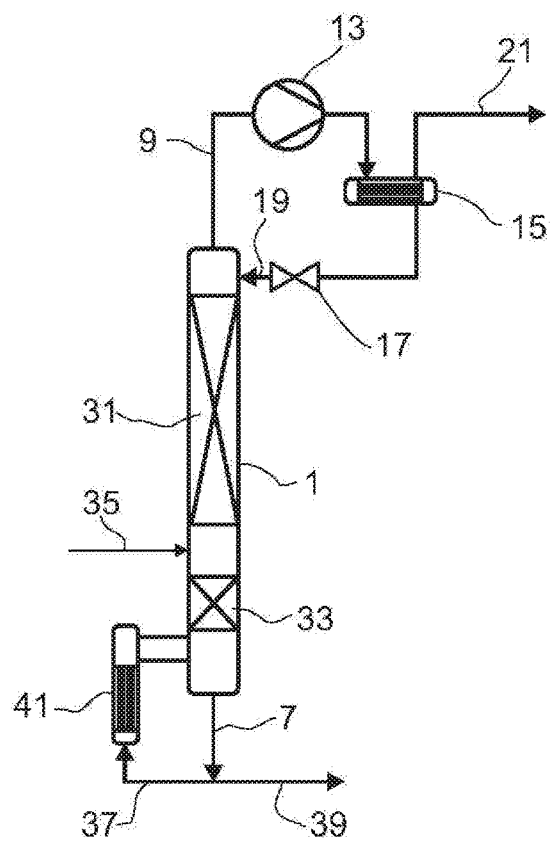
FIG. 4 shows the method according to the invention in a distillation column with a rectifying section and a stripping section.

A stream substantially free of hydrogen chloride may be obtained at the bottom by operating distillation column 1 not as a pure rectifying column as in the embodiments depicted in FIGS. 1 to 3 but as distillation column 1 comprising rectifying section 31 and stripping section 33. A corresponding embodiment is depicted in FIG. 4. When distillation column 1 comprises rectifying section 31 and stripping section 33, feed 5 for the phosgene- and hydrogen chloride-comprising stream is disposed not in lower region 3 of the distillation column but between rectifying section 31 and stripping section 33 as side feed 35.

In this case it is further advantageous when the stream withdrawn via bottom takeoff 7 is divided into first bottoms substream 37 and second bottoms substream 39. The fraction of this first substream 37 based on the entire stream withdrawn via bottom takeoff 7 depends on the reflux and the type of evaporator employed. First bottoms substream 37 is supplied to evaporator 41, in which said substream at least partially evaporates, and subsequently returned to lower region 3 of distillation column 1.

Here too, it is possible to pre-cool and/or partially condense the phosgene- and hydrogen chloride-comprising stream to be supplied, as in the FIG. 3 embodiment, and/or to introduce into the compressor and subsequently into the top condenser not the entire essentially hydrogen chloride-comprising stream withdrawn via top takeoff 9 but only a substream of the essentially hydrogen chloride-comprising stream withdrawn via top takeoff 9 as in the FIG. 2 embodiment.

Figure 5:
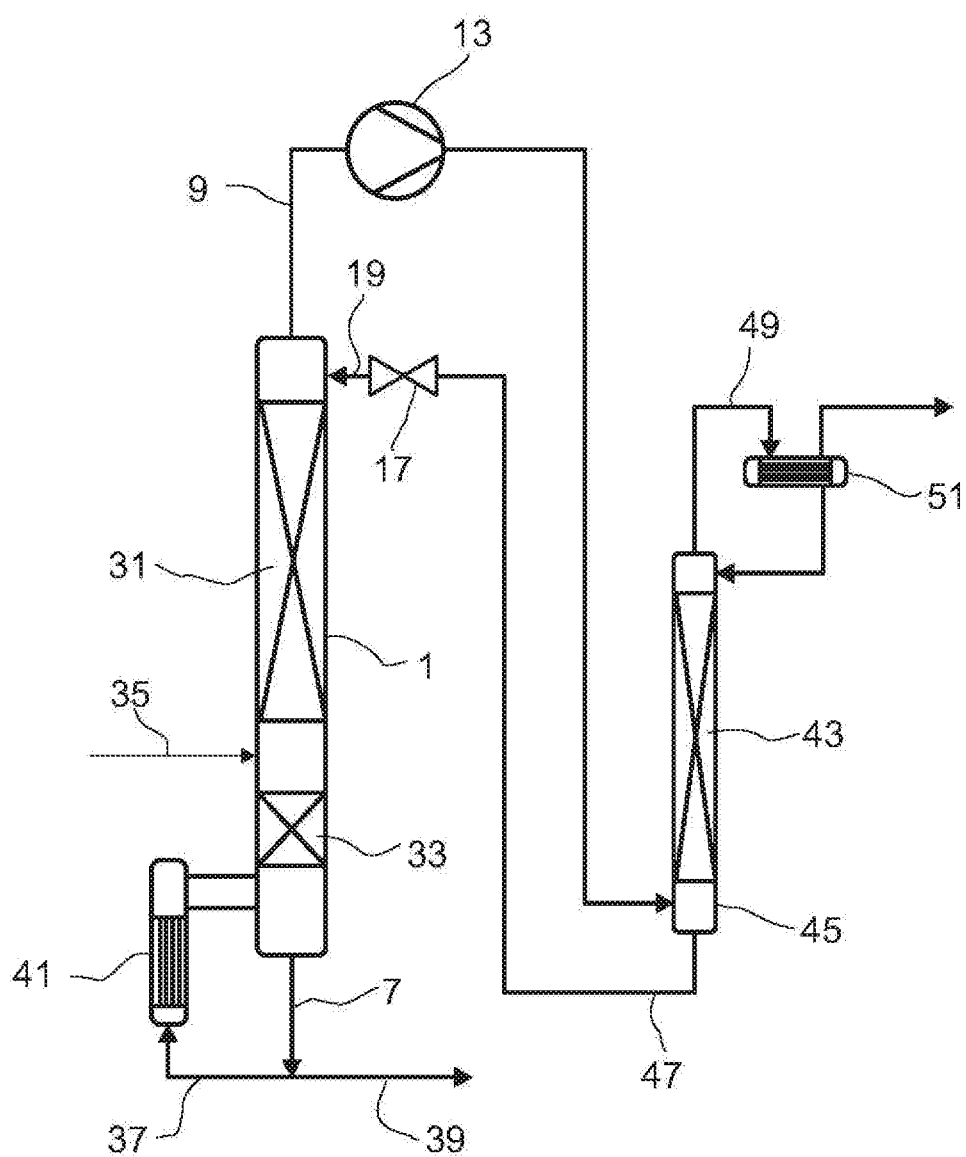
FIG. 5 shows the method according to the invention with an additional rectifying column.

The method depicted in FIG. 5 differs from the method depicted in FIG. 4 in that it comprises additional rectifying column 43. Additional rectifying column 43 makes it possible to concentrate the essentially hydrogen-chloride comprising stream yet further and remove impurities, for example phosgene, still present in the essentially hydrogen chloride-comprising stream withdrawn via top takeoff 9.

Rectifying column 43 is connected downstream of compressor 13 and the essentially hydrogen chloride-comprising stream is therefore introduced into rectifying column 43 after compression in compressor 13. The feed for this compressed essentially hydrogen chloride-comprising stream is in lower region 45 of rectifying column 43, preferably below any internals, for example trays, a structured packing or a random packing, in rectifying column 43. Rectifying column 43 affords a bottoms stream which is withdrawn via bottom takeoff 47 and decompressed in decompression means 19. The bottoms stream obtained at bottoms takeoff 47 of rectifying column 43 is subsequently recycled into the top of distillation column 1.

The stream obtained at the top of rectifying column 43 is withdrawn via top takeoff 49 and introduced into top condenser 51. The stream obtained at the top of rectifying column 43 is partially condensed in top condenser 51. The condensed, liquid portion is recycled into the top of rectifying column 43 and the uncondensed gaseous portion is discharged and, for example, sent for use in hydrochloric acid production or oxidation of hydrogen chloride for chlorine production.

In the FIG. 5 embodiment too, it is possible to pre-cool and/or partially condense the supplied phosgene- and hydrogen chloride-comprising stream before it is conveyed into the distillation column and/or to supply only a substream to the compressor. In this case it is particularly advantageous when the entire stream withdrawn at the top of distillation column 1 is supplied to compressor 13 and subsequently to rectifying column 43.

Figure 6:
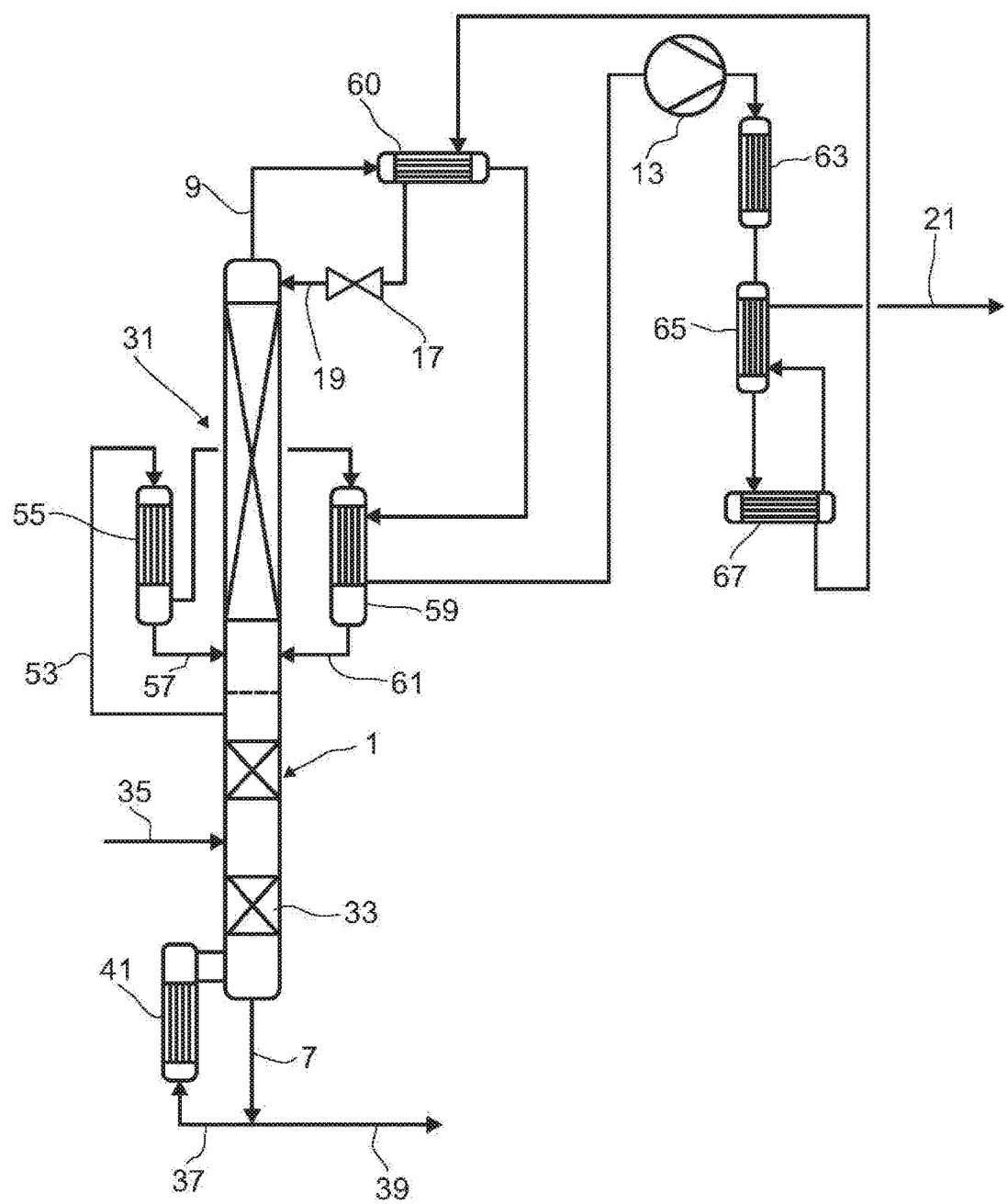
FIG. 6 shows the method according to the invention with additional heat integration measures.

FIG. 6 shows the method according to the invention with additional heat integration measures.

In a first heat integration measure, a gas stream is withdrawn from rectifying section 31 of distillation column 1 via side takeoff 53. In order that the gas stream may be withdrawn, in the embodiment shown here the rectifying section 31 comprises two separate internals. Side takeoff 53 is disposed between these separate internals of rectifying section 31.

Once withdrawn via side takeoff 53, the gas stream is supplied to first condenser 55. The gas stream is partially condensed in first condenser 55. The liquid portion is supplied via first side feed 57, preferably between the internals of the rectifying section. The uncondensed portion is supplied to second condenser 59. In accordance with the invention, first condenser 55 is operated with an external energy supply. In this embodiment, top stream 9 is initially supplied to heat transferor 60. The essentially hydrogen chloride-comprising stream exiting heat transferor 60 is utilized in second condenser 59 to further condense the gaseous portion. The stream partially condensed in this way is recycled into distillation column 1 via second side feed 61, preferably at the same height as first side feed 57. Nevertheless, first side feed 57 and second side feed 61 may also be disposed at different heights. However, it is also preferable in this case when first side feed 57 and second side feed 61 are disposed above side takeoff 53 and between the internals of rectifying section 31.

The giving-out of heat from the stream which is to be partially condensed causes the essentially hydrogen chloride-comprising stream to absorb heat from the top of the column in second condenser 59. Once it has exited second condenser 59, the essentially hydrogen chloride-comprising stream is supplied to compressor 13 and compressed to a higher pressure. The compressed stream is cooled down in first cooler 63 and then supplied to second cooler 65 and finally to condenser 67. The essentially hydrogen-chloride comprising stream is partially condensed in condenser 67. The liquid portion is supplied to heat transferor 60 as heat-transfer medium. In heat transferor 60, the liquid portion gives off heat to the essentially hydrogen chloride-comprising stream withdrawn via top takeoff 9 and thus heats said stream. The heated essentially hydrogen chloride-comprising stream is then supplied—as described hereinabove—to second condenser 59. The liquid portion cooled down further in heat transferor 60 is decompressed in decompression means 17 and returned into the top of distillation column 1.

The gaseous portion withdrawn from condenser 67 is introduced into second cooler 65 as coolant and the gaseous portion thus absorbs heat from the compressed and essentially hydrogen chloride-comprising stream that is to be condensed, this absorption of heat occurring before said stream is introduced into condenser 67. The portion heated in the second cooler is withdrawn from the process via gas takeoff 21.

In addition to the coupling of the heat integration measures shown in FIG. 6, said measures may also be employed in any desired other combination or else only individually. It is further possible—as shown in FIG. 3—to pre-cool and/or partially condense the phosgene- and hydrogen chloride-comprising stream before it is conveyed into distillation column 1.

In some versions of the method it may be advantageous to carry out compression as a multi-stage procedure using intermediate cooling where necessary.

EXAMPLES

Comparative Example

The bottom of an absorption column is supplied with 35 000 kg/h of a stream comprising 28.6 wt % of hydrogen chloride, 62.9 wt % of phosgene and 8.6 wt % of chlorobenzene at a temperature of 90° C. and the top of said column is supplied with 11254 kg/h of chlorobenzene at a temperature of −25° C. The chlorobenzene and the stream comprising hydrogen chloride, phosgene and chlorobenzene are run in countercurrent. At the bottom of the absorption column, 37670 kg/h of a stream comprising 3.8 wt % of hydrogen chloride (1431 kg/h), 58.4 wt % of phosgene and 37.8 wt % of chlorobenzene is obtained at a temperature of −7.6° C. The stream obtained at the top of the distillation column is partially condensed in a condenser, the condensed portion is recycled into the absorption column and the gaseous portion is withdrawn from the process. The gaseous fraction has a flow rate of 8584 kg/h, comprises 99.8 wt % of hydrogen chloride and 0.1 wt % of each of phosgene and chlorobenzene and has a temperature of −25° C. The absorption is carried out at a pressure of 2.2 bar.

Example

Work-up of the stream comprising hydrogen chloride, phosgene and chlorobenzene was performed using a distillation column corresponding to the set-up depicted in FIG. 3 instead of an absorption column as used in the comparative example. The composition of the stream supplied to this distillation column is the same as the composition in the comparative example.

A flow rate of 35 000 kg/h of the stream comprising hydrogen chloride, phosgene and chlorobenzene at a temperature of 90° C. affords 26212 kg/h of a stream comprising 4.7 wt % of hydrogen chloride (1232 kg/h), 83.9 wt % of phosgene and 11.4 wt % of chlorobenzene at the bottom of the distillation column at a temperature of −15.4° C. The distillation is carried out at a pressure of 2.2 bar.

The gas stream obtained at the top is compressed to a pressure of 13.2 bar and supplied to the top condenser. The condensed liquid substream is expanded and recycled into the distillation column. The gas stream is withdrawn at a temperature of −22.8° C. The gas stream withdrawn from the top condenser has a flow rate of 8788 kg/h and comprises 99.9 wt % of hydrogen chloride and 0.1 wt % of phosgene.

In contrast with the absorption, the phosgene-comprising stream obtained at the bottom comprises very much less solvent and also less hydrogen chloride. Further work-up of this stream prior to reuse in the reaction may either be dispensed with or else simplified considerably. The gas stream downstream of the top condenser is free of solvent and said gas stream may therefore be sent, for example, to an oxidative dehydration (Deacon process) or an HCl electrolysis without further work-up.

LIST OF REFERENCE NUMERALS

1 Distillation column
3 Lower region of distillation column 1
5 Feed
7 Bottom takeoff
9 Top takeoff
11 Internals
13 Compressor
15 Top condenser
17 Decompression means
19 Return line to top of column
21 Gas takeoff
23 First substream
25 Second substream
27 Second decompression means
29 Heat exchanger
31 Rectifying section
33 Stripping section
35 Side feed
37 First bottoms substream
39 Second bottoms substream
41 Evaporator
43 Rectifying column
45 Lower region of rectifying column 43
47 Bottom takeoff of rectifying column 43
49 Top takeoff of rectifying column 43
51 Top condenser of rectifying column 43
53 Side takeoff
55 First condenser
57 First side feed
59 Second condenser
60 Heat transferor
61 Second side feed
63 First cooler
65 Second cooler
67 Condenser

The invention claimed is:

1. A method of separating a phosgene- and hydrogen chloride-comprising stream comprising:
conveying the hydrogen chloride- and phosgene-comprising stream into a distillation column,
withdrawing at the bottom of the distillation column a phosgene-comprising stream, and
withdrawing at the top of the distillation column an essentially hydrogen chloride-comprising stream,
wherein at least a portion of the essentially hydrogen-chloride comprising stream withdrawn at the top is compressed and at least partially condensed and at least a portion of the partially condensed liquid and compressed essentially hydrogen chloride-comprising stream is decompressed and recycled into the top of the distillation column as reflux.

2. The method according to claim 1, wherein the essentially hydrogen chloride-comprising stream is withdrawn at the top at a pressure in the range of from 1 to 10 bar and is compressed to a pressure in the range of from 5 to 25 bar before condensation.

3. The method according to claim 1, wherein the distillation column comprises a rectifying section and a stripping section and the phosgene- and hydrogen chloride-comprising stream is supplied as a side feed between the rectifying section and the stripping section.

4. The method according to claim 1, wherein after compression the essentially hydrogen chloride-comprising stream withdrawn from the top is supplied to a rectifying column and the stream obtained at the bottom of the rectifying column is recycled into the top of the distillation column.

5. The method according to claim 1, wherein in a heat exchanger the at least partially condensed and essentially hydrogen chloride-comprising stream gives off heat to the hydrogen chloride-comprising stream that is to be condensed, this giving-off of heat occurring before said stream is compressed.

6. The method according to claim 1, wherein in a heat exchanger the uncondensed portion of the essentially hydrogen chloride-comprising stream absorbs heat from the compressed and hydrogen chloride-comprising stream that is to be condensed.

7. The method according to claim 1, wherein a gas stream is withdrawn from the distillation column via a side takeoff, said stream is at least partially condensed in a first cooler, a liquid fraction is recycled into the distillation column and a gaseous portion is supplied to a second cooler, wherein in the second cooler the gas stream gives off heat to the essentially hydrogen chloride-comprising stream withdrawn from the top.

8. The method according to claim 7, wherein the essentially hydrogen chloride-comprising stream withdrawn from the top is heated up in a heat exchanger before being fed into the second cooler.

9. The method according to claim 8, wherein in the heat the essentially hydrogen chloride-comprising stream withdrawn from the top absorbs heat from the condensed stream recycled into the top of the distillation column.

* * * * *